US 6,579,268 B1

(12) United States Patent
Loining

(10) Patent No.: US 6,579,268 B1
(45) Date of Patent: Jun. 17, 2003

(54) CATHETER SUPPORT POUCH

(76) Inventor: Michelle J. Loining, 1980 Tunis Rd., Green Bay, WI (US) 54311

( * ) Notice: Subject to any disclaimer, the term of this patent is extended or adjusted under 35 U.S.C. 154(b) by 0 days.

(21) Appl. No.: 10/057,101

(22) Filed: Oct. 25, 2001

(51) Int. Cl.[7] ............................................... A61M 5/32
(52) U.S. Cl. ........................................ 604/174; 604/179
(58) Field of Search .............................. 604/179, 174, 604/178, 175, 331, 343, 345; 128/DIG. 26

(56) References Cited

U.S. PATENT DOCUMENTS

| | | | |
|---|---|---|---|
| 4,574,798 A | * 3/1986 | Heitzman ............. 128/205.22 |
| 4,578,062 A | 3/1986 | Schneider |
| 4,582,508 A | 4/1986 | Pavelka |
| 4,596,560 A | 6/1986 | Simpson |
| 4,605,397 A | * 8/1986 | Ligon et al. ............... 604/179 |
| 4,666,432 A | 5/1987 | McNeish et al. |
| 4,671,787 A | * 6/1987 | Widman .................... 604/179 |
| 4,799,923 A | 1/1989 | Campbell |
| 4,973,314 A | 11/1990 | Garrett |
| 5,048,512 A | 9/1991 | Turner et al. |
| 5,205,832 A | * 4/1993 | Tuman ....................... 604/179 |
| 5,334,186 A | * 8/1994 | Alexander .................. 604/180 |
| 5,403,285 A | 4/1995 | Roberts |
| 5,624,403 A | * 4/1997 | Jaquith ....................... 604/179 |
| 5,643,236 A | * 7/1997 | Hadley ....................... 604/353 |
| 5,688,248 A | 11/1997 | Lessing, Jr. |
| 5,700,257 A | * 12/1997 | Minick et al. ............. 604/408 |
| 5,709,665 A | 1/1998 | Vergano et al. |
| 5,755,698 A | * 5/1998 | Kagan et al. ............... 604/179 |
| 5,853,396 A | * 12/1998 | Bennes et al. ............. 604/179 |
| 6,206,854 B1 | 3/2001 | Weaver |
| 6,247,211 B1 | * 6/2001 | Bell ........................... 24/306 |
| 6,279,580 B1 | * 8/2001 | Perez et al. ................ 128/897 |
| 6,436,074 B1 | * 8/2002 | Lee ............................ 604/174 |

* cited by examiner

Primary Examiner—Sharon Kennedy
(74) Attorney, Agent, or Firm—Boyle Fredrickson Newholm Stein & Gratz S.C.

(57) ABSTRACT

A pouch for releasably securing a free end of a catheter extending outwardly from the body of an individual in a concealed position on the body of the individual. The pouch is formed of a fabric or material. At one end, the pouch includes a releasable clip adapted to secure the pouch to an article of clothing worn by the individual in a position where the pouch is concealed. The pouch also includes at least one releasable closure that enables the patient to selectively open and close the pouch in order to insert and remove the free end of the catheter from the pouch.

20 Claims, 3 Drawing Sheets

FIG.

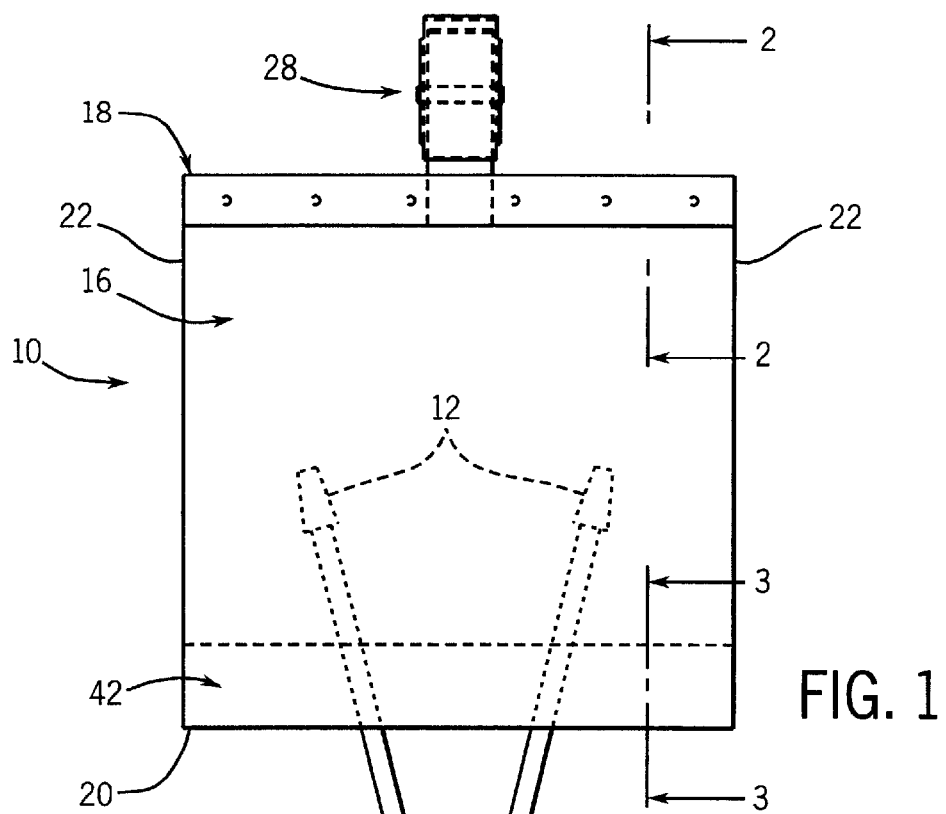
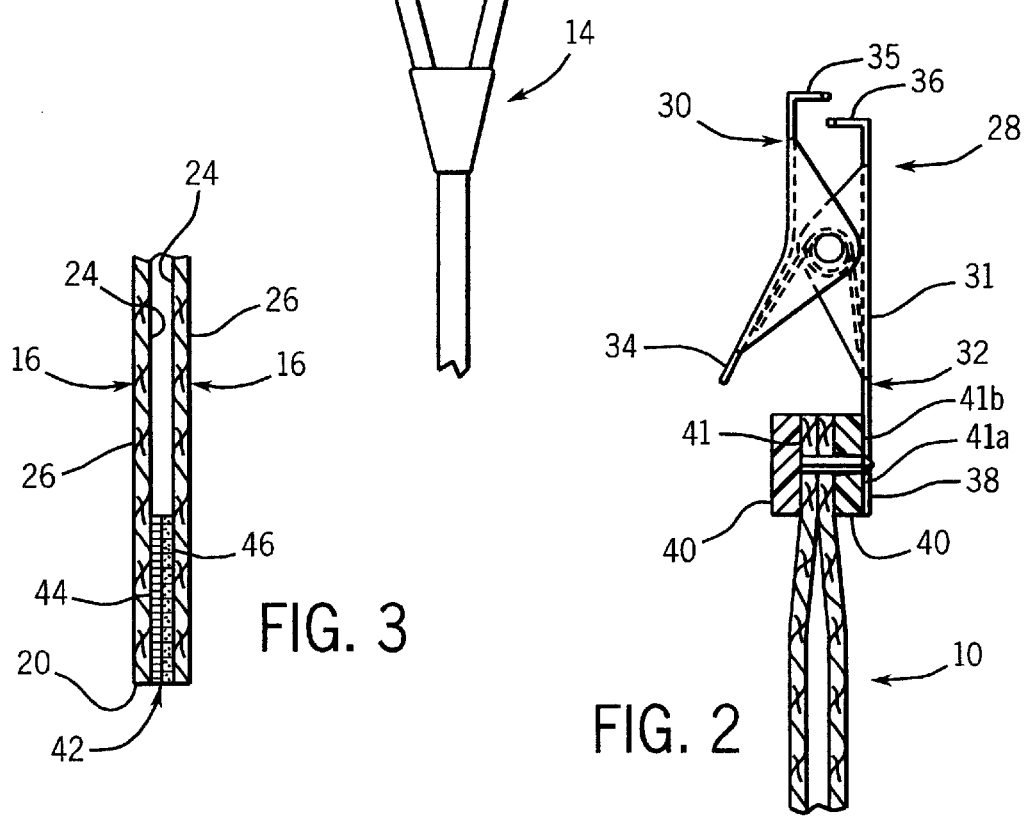

CATHETER SUPPORT POUCH

FIELD OF THE INVENTION

The present invention relates to a pouch for supporting a free end of a catheter on a patient from which the catheter extends, and more specifically to a releasably securable pouch capable of holding the free end of a catheter in a concealed location on a desired part of the clothing worn by the patient.

BACKGROUND OF THE INVENTION

As a result of various medical procedures, it is necessary to implant a catheter in the body of a patient in order to drain bodily fluids from the patient or to facilitate the connection of the part of the body to which the catheter is connected to a machine, such as a dialysis machine. As a result, after these procedures have been completed, the implanted catheters have a free end that extends outwardly through the skin of the patient for these purposes.

The free end of the catheter extending outwardly from the patient's body often causes problems for the patient when attempting to carry out normal daily activities. For example, the free end of the catheter can catch or snag on object that the patient walks by or on articles of clothing the patient is wearing. It is imperative that the catheter be prevented from catching on any objects or articles of clothing the patient may wear to ensure that the incision through which the catheter extends into the body is not ruptured or enlarged by the catheter pulling on an edge of the incision. Furthermore, constant rubbing or movement of the catheter within the incision irritates the skin around the incision, causing significant discomfort to the patient.

In the prior art, a number of different types of supports have been developed to receive and secure the exposed free end of a catheter extending from the body of a patient. In many cases, these supports take the form of bags having elongate straps which are releasably positionable about the head, shoulders and/or waist of the patient such that the bag can be supported on the body of the patient in a manner similar to that used for supporting a purse, backpack or belt. While these devices are effective in maintaining the position of the catheter with respect to the patient to avoid discomfort and irritation caused by movement of the catheter, the overall structure forming the support is bulky and makes it difficult for the user to readily conceal the existence of the catheter.

Other types of prior art catheter supports take the form of pocket-like dressings which are adhereable directly to the skin of the patient. While better able to conceal the presence of the catheter, these types of supports cannot be moved to different locations on the patient after the initial application to the patient. Therefore, the catheter cannot be moved in order to accommodate for the particular article of clothing worn by the patient in order to effectively conceal the catheter.

Therefore, it is desirable to develop a catheter support pouch which can reliably, releasably and comfortably hold the catheter in a stationary position on the patient while the patient is ambulatory to avoid irritation of or damage to the incision, but that also is positionable in a non-obvious location on a patient to effectively conceal the presence of the catheter.

SUMMARY OF THE INVENTION

It is an object of the present invention to provide a catheter support pouch that is easily opened and closed in order to selectively insert and remove an exposed, free end of a catheter from the pouch.

It is another object of the invention to provide a catheter support pouch that can be easily and releasably attached to an article of clothing worn by the patient using a suitable securing means.

It is still another object of the invention to provide a catheter support pouch which can be easily concealed beneath the clothing worn by the patient to effectively conceal the presence of the catheter.

It is still a further object of the invention to provide a catheter support pouch that is formed of hypoallergenic and inexpensive materials such that the pouch is inexpensive to manufacture and can be discarded after use.

The present invention is a catheter support pouch capable of releasably securing an exposed, free end of a catheter extending out of a patient's body on any desired portion of clothing worn by the patient. The pouch is formed of a pair of panels of fabric material which are connected to one another to form a pouch having an open interior. The pouch includes a releasable closure at one end that allows the pouch to be selectively opened and closed in order to receive and retain the free end of the catheter. The pouch also includes a releasable securing means attached to the pouch that enables the pouch to be secured to any article of clothing worn by the patient such that the pouch, and the presence of the catheter, are effectively concealed.

Various other features, objects and advantages of the invention will be made apparent from the following detailed description taken together with the drawings.

BRIEF DESCRIPTION OF THE DRAWINGS

The drawings illustrate the best mode presently contemplated of carrying out the invention.

In the drawings:

FIG. 1 is a front plan view of the catheter support pouch of the present invention;

FIG. 2 is a cross-sectional view along line 2—2 of FIG. 1;

FIG. 3 is a cross-sectional view along line 3—3 of FIG. 1;

DETAILED DESCRIPTION OF THE INVENTION

Figure 7:
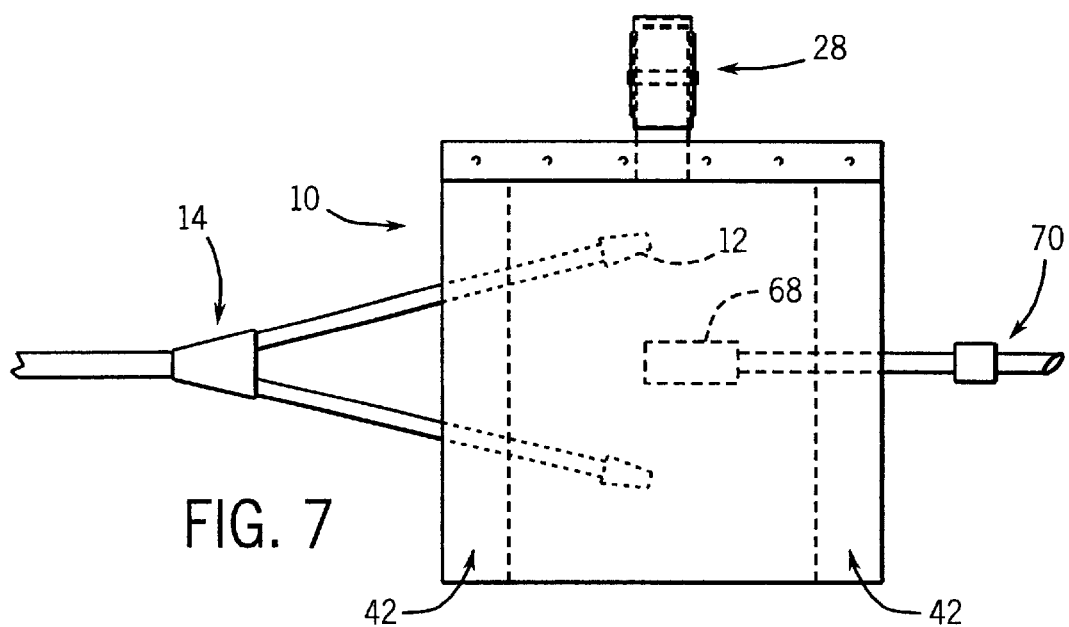
FIG. 7 is a front plan view of a fourth embodiment of the pouch of FIG. 1.

With respect now to the drawing figures in which like reference numerals designate like parts throughout the disclosure, a catheter support pouch is indicated generally at 10 in FIG. 1. The pouch 10 is used to receive and retain a free end or ends 12 of a catheter 14 extending from within the body of a patient, such as a Hickman catheter.

The pouch 10 is formed of a pair of material pieces 16 secured to one another and includes a top end 18 spaced opposite a bottom end 20 and a pair of sides 22 extending between the top end 18 and bottom end 20. The pieces 16 each include an interior face 24 and an exterior face 26 and are positioned with respect to one another to form the pouch 10 by placing the interior faces 24 adjacent one another. The material pieces 16 are then secured to one another to form the sides 22 of the pouch 10. The pieces 16 may be secured to one another by any suitable means, such as thread, adhesives or other conventional bonding techniques. The pieces 16 can be secured to one another in any of the previously mentioned ways due to the fact that the pieces 16 are formed of a suitable fabric material, such as polyester, cotton or flannel, with the preferred material being a medical quality fabric formed of 65% polyester and 35% cotton.

Once the pieces 16 are secured to one another along the sides 22, a clip 28 can be permanently secured to the top end 18 of the pouch 10. As best shown in FIG. 2, the clip 28 can be any conventional type of clip, such as a spring-biased or over-center locking clip, formed of a generally rigid material such as a metal or a hard plastic, but preferably is a spring-biased releasable clip including a first arm 30 pivotally secured to a second arm 32, a spring 31 disposed between the first arm 30 and second arm 32 and a manually operable handle 34 extending from the first arm 30. The first arm 30 and second arm 32 each include projections 35 and 36, respectively, that extend inwardly towards one another. The spring 31 biases the first arm 30 towards the second arm 32 so that the projections 35 and 36 are positioned adjacent one another to engage a portion of clothing worn by the patient. By pivoting the handle 34 toward the second arm 32 when the clip 28 is in the position shown in FIG. 2, the handle 34 urges the first arm 30 away from the second arm 32 to place the clip 28 in an open position in order to release any clothing positioned between the projections 35 and 36 on the first arm 30 and second arm 32, respectively.

Opposite the projection 36, the second arm 32 also includes a flange 38 used to secure the second arm 32 to the pouch 10. The flange 38 can be secured to the top end 16 of the pouch 10 by any suitable means. For example, the flange 38 can be adhered directly to the interior faces 24 of each material piece 16. Also, the top end 18 can be sewn closed around the flange 38. The flange 38 can also be secured directly to the exterior faces 26 of the material pieces 16 to retain the clip 28 on the top end 18. However, the clip 28 is preferably retained on the top end 18 by engagement of the flange 38 with a pair of plastic strips 40 that are engaged with one another on opposite sides of the top end 18 of the pouch 10. The strips 40 include opposed portions of a securement mechanism 41 that can be any conventional interlocking mechanism, such as a snapping mechanism but preferably has a number of pins 41a extending from one strip 40 and a number of aligned openings 41b in the opposite strip 40. The pins 41a can be pressed through the pieces 16 into engagement within the openings 41b to enable the strips 40 to be secured to one another. The pins 41a can be secured within the openings by any conventional means. For example, the pins 41a can include projections (not shown) that engage the openings 41b after insertion of the pins, or an adhesive can be placed within the openings 41b to adhere the pins 41a within the openings.

The clip 28 is secured to one of the plastic strips 40 by attaching the flange 38 on the second arm 32 using any suitable means, such as an adhesive or by engaging the mechanism 41 with the flange 38. The flange 38 can be secured to the outside of the strip 40, as shown in FIG. 2, or to the interior of the strips 40.

By securing the clip 28 to the top end 16, the clip 28 can be utilized to support the pouch 10 on a patient by engaging the clip 28 to an article of clothing that the patient is wearing such that the pouch 10 hangs downwardly from the clothing. Furthermore, based on the construction of the clip 28, the pouch 10 can be secured to an interior side of the clothing worn by the patient such that the pouch 10 can be readily concealed by the clothing.

Referring again to FIG. 1, the bottom end 20 of the pouch 10 includes a releasable closure 42 disposed on the interior faces 24 of each material piece 16. The closure 42 enables the bottom end 20 to be releasably opened and closed in order to selectively insert and remove the free end 12 of the catheter 14 from within the pouch 10. The closure 42 is formed of a hook strip 44 positioned on the interior face 24 of one of the material pieces 16 and a loop strip 46 positioned on the interior face 24 of the opposite material piece 16. When the hook strip 44 and loop strip 46 are engaged with one another to close the pouch 10 and retain the free end 12 of the catheter 14 within the pouch 10, the strips 44 and 46 forming the closure 42 deform and conform to the shape of the catheter 14 positioned between the strips 44 and 46 such that the catheter 14 is not damaged by the closure 42.

Figure 4:
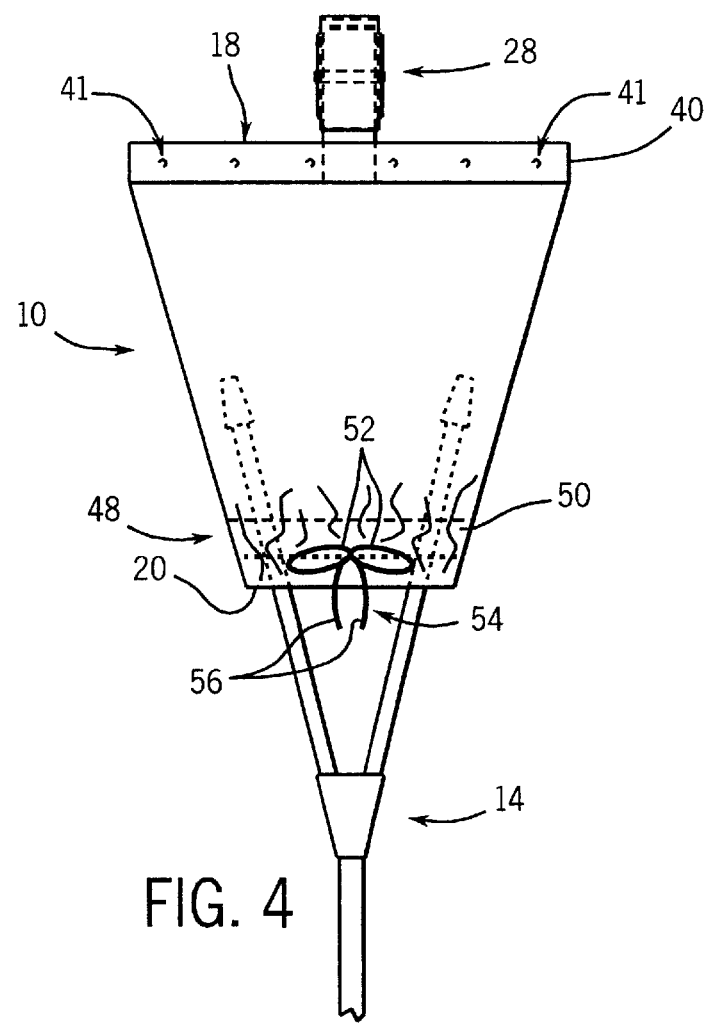
FIG. 4 is a front plan view of a second embodiment of the pouch of FIG. 1.

Referring now to FIG. 4, as an alternative to the closure 42 formed of the strips 44 and 46, the pouch 10 may include a drawstring closure arrangement 48 positioned at the bottom end 20 of the pouch 10. To form the arrangement 48, the ends of each material piece 16 forming the bottom end 18 are folded inwardly toward the top end 18 and secured to the interior face 24 of each material piece 16 to form a channel 50 on each side of the bottom end 20. The channels 50 extend the length of each side of the bottom end 20 of the pouch 10 and include one of a pair of adjacent openings 52 extending through the material pieces 16. A drawstring 54 having a pair of opposed ends 56 is inserted through the channels 50 such that each of the ends 56 extends outwardly from the channels 50 through one of the openings 52. After inserting the free end 12 of the catheter 14 into the pouch 10, the opposed ends 56 of the drawstring 54 can be pulled outwardly to constrict the channel 50 and bottom end 20 to releasably secure the free end 12 within the pouch 10. The bottom end 20 can be maintained in a closed position by tying the opposed ends 56 of the drawstring 54 to one another, which also enables the bottom end 20 to be easily reopened by subsequently untying the opposed ends 56.

Figure 5:
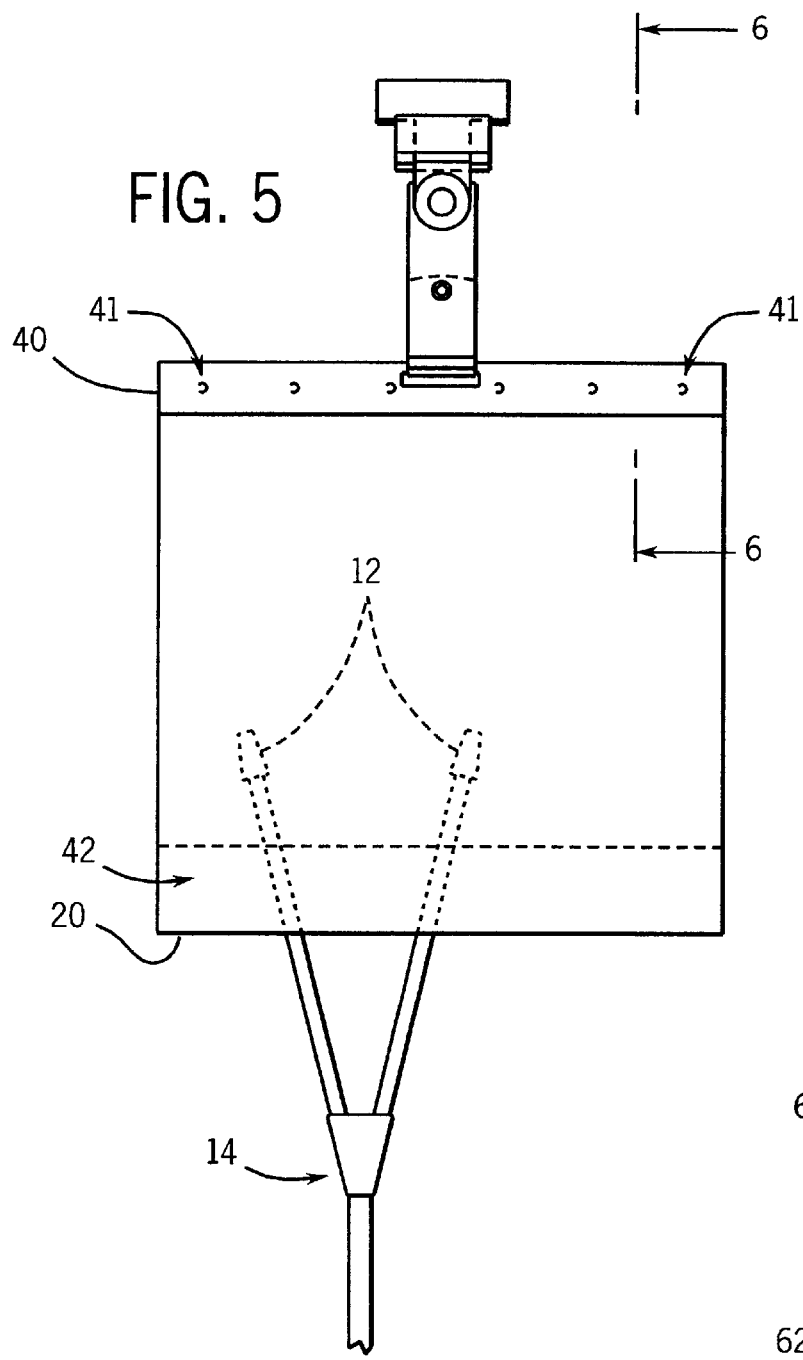
FIG. 5 is a front plan view of a third embodiment of the pouch of FIG. 1.
Figure 6:
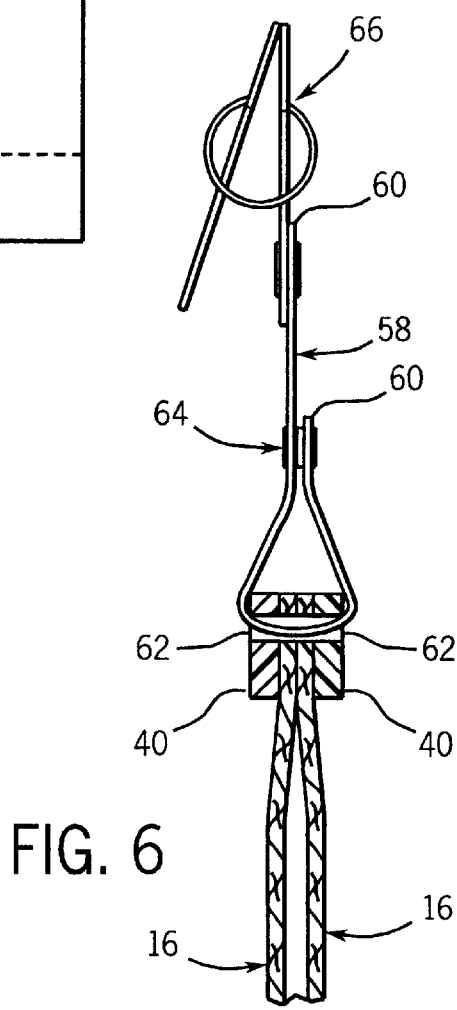
FIG. 6 is a cross-sectional view along line 6—6 of FIG. 5.

As shown in FIGS. 5 and 6, in another embodiment of the pouch 10, a strap 58 having a pair of opposed ends 60 is inserted through an opening 62 in each of the strips 40 adjacent the top end 18. The strap 58 includes a snap arrangement 64 disposed on the strap 58 that is used to releasably retain the strap 58 within the opening. On one end 60 of the strap is disposed a bulldog clip 66 that can be used to releasably secure the pouch 10 to a garment of the individual. Furthermore, because the pouch 10 is manufactured to be disposable after use, in this embodiment, the strap 58 and clip 66 can be removed from the pouch 10 by disengaging the snap arrangement 64 and reused with another pouch 10.

In order to accommodate a patient with more than one catheter 12 extending from the body of the patient, the pouch 10 can also be adapted to the configuration shown in FIG. 7. In this embodiment, the bottom end 20 of the pouch 10 is closed, and the sides 22 of each piece 16 are not attached to one another. A pair of closures 42 are positioned along the interior of each side 22 such that the pouch 10 includes a pair of open sides 68 on opposite sides of the pouch 10. The closures 42 enable each side 22 to be selectively opened and closed to receive the free end 14 of a catheter 12 as well as the free end 68 of a tube 70, such as an IV tube.

Various alternatives and embodiments are contemplated as being within the scope of the following claims particularly pointing out and distinctly claiming the subject matter regarded as the invention.

I claim:

1. A pouch for releasably supporting a medical device on the body of an individual, the pouch comprising:
    a) a pair of fabric pieces secured to one another;
    b) a first closure positioned at one end of each fabric piece;
    c) a second closure positioned opposite the first closure; and
    d) a releasable clip attached to the pouch.

2. The pouch of claim 1 wherein the clip is attached to the first closure.

3. The pouch of claim 1 wherein the second closure is a releasable closure.

4. The pouch of claim 3 wherein the first closure is a releasable closure.

5. The pouch of claim 3 wherein the second closure is formed of releasably engageable hook and loop panels.

6. The pouch of claim 3 wherein the second closure is formed of a number of snap closures.

7. The pouch of claim 3 wherein the second closure is formed of a drawstring arrangement.

8. The pouch of claim 1 wherein the first closure is a non-releasable closure.

9. The pouch of claim 8 wherein the first closure is stitching.

10. The pouch of claim 8 wherein the first closure is at least one hard plastic strip secured to the pouch.

11. The pouch of claim 1 wherein the fabric pieces are formed of plastic.

12. The pouch of claim 11 wherein the fabric pieces are formed of polyester.

13. The pouch of claim 1 wherein the fabric pieces are formed of cotton.

14. The pouch of claim 1 wherein the fabric pieces are formed of polyester and cotton.

15. The pouch of claim 1 wherein the clip is formed of plastic.

16. The pouch of claim 1 wherein the fabric pieces are integrally formed with one another along one of the sides.

17. A method for securing a free, exposed end of a catheter tube extending from an individual to the individual, the method comprising the steps of:
    a) providing a pouch formed of a pair of fabric pieces secured to one another, the pouch including a releasable closure and a clip attached to the pouch for releasably securing the pouch to the individual;
    b) opening the releasable closure;
    c) inserting a free end of the catheter into the pouch through the releasable closure;
    d) closing the releasable closure around the free end of the catheter; and
    e) securing the pouch to the individual.

18. The method of claim 17 wherein the step of securing the pouch to the individual comprises the steps of:
    a) opening the clip;
    b) placing the clip against clothing worn by the individual; and
    c) closing the clip around a section of clothing.

19. The method of claim 17 wherein the clip includes a pair of separable portions and the step of securing the pouch to the individual comprises the steps of:
    a) separating the portions of the clip;
    b) placing the section of the clothing between the portions; and
    c) closing the portions around the section of clothing.

20. The method of claim 19 further comprising the step of removing the pouch from the individual after securing the pouch to the individual.

* * * * *